United States Patent [19]

Gregson et al.

[11] 4,446,317
[45] * May 1, 1984

[54] CEPHALOSPORIN ANTIBIOTICS

[75] Inventors: Michael Gregson, Middlesex; Richard B. Sykes, Chalfont St Giles, both of England

[73] Assignee: Glaxo Operations U.K. Limited, London, England

[*] Notice: The portion of the term of this patent subsequent to May 12, 1998 has been disclaimed.

[21] Appl. No.: 343,326

[22] Filed: Jan. 27, 1982

Related U.S. Application Data

[63] Continuation of Ser. No. 176,520, Aug. 8, 1980, abandoned, which is a continuation of Ser. No. 61,259, Jul. 27, 1979, abandoned, which is a continuation of Ser. No. 921,119, Jun. 30, 1978, abandoned, which is a continuation of Ser. No. 768,719, Feb. 15, 1977, abandoned.

[30] Foreign Application Priority Data

Feb. 16, 1976 [GB] United Kingdom ............... 6010/76
Jul. 30, 1976 [GB] United Kingdom ............. 27300/76

[51] Int. Cl.$^3$ ..................................... C07D 501/34
[52] U.S. Cl. ........................................... 544/22
[58] Field of Search ..................................... 544/22

[56] References Cited

U.S. PATENT DOCUMENTS

| | | | |
|---|---|---|---|
| 3,962,227 | 6/1976 | Chauvette | 544/22 |
| 3,974,153 | 8/1976 | Cook et al. | 424/246 |
| 4,267,320 | 5/1981 | Gregson et al. | 544/22 |

FOREIGN PATENT DOCUMENTS 2405877 2/1974 Fed. Rep. of Germany.

Primary Examiner—Paul M. Coughlan, Jr.
Attorney, Agent, or Firm—Bacon & Thomas

[57] ABSTRACT

The invention provides novel antibiotic cefuroxime esters of the formula

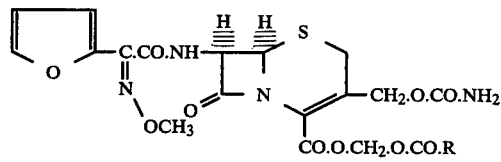

(wherein R is a primary or secondary alkyl group containing 1 to 4 carbon atoms). These compounds are useful as orally administrable broad spectrum antibiotics.

6 Claims, No Drawings

CEPHALOSPORIN ANTIBIOTICS

This application is a continuation, of application Ser. No. 176,520, filed Aug. 8, 1980. Which is a continuation of Ser. No. 061,259, filed July 27, 1979, which is a continuation of 921,119, filed June 30, 1978, which in turn is a continuation of 768,719, filed on Feb. 15, 1977, all now abandoned.

This invention is concerned with improvements in or relating to cephalosporin antibiotics. More particularly the invention is concerned with biologically acceptable ester derivatives of (6R,7R)-3-carbamoyloxymethyl-7-[(Z)-2-(fur-2-yl)-2-methoxyiminoacetamido]ceph-3-em-4-carboxylic acid (i.e. the syn isomer), which has the approved name "cefuroxime".

Cefuroxime, as disclosed in British Pat. No. 1,453,049 as a valuable broad spectrum antibiotic characterised by high activity against a wide range of gram-positive and gram-negative microorganisms, this property being enhanced by the very high stability of the compound to $\beta$-lactamases produced by a range of gram-negative microorganisms. Additionally the compound is stable in the body owing to its resistance to the action of mammalian esterases, and gives high serum levels following parenteral administration (e.g. in the form of the sodium salt) to human and animal subjects, while exhibiting low serum binding.

Cefuroxime and its salts, for example alkali metal salts such as the sodium salt, are principally of value as injectable antibiotics since they are poorly absorbed from the gastro-intestinal tract and are therefore present in sera and urine only in low concentrations after oral administration. We have accordingly conducted extensive studies into the possible activity upon oral administration of various derivatives of cefuroxime, since the development of derivatives which are absorbed through the gastro-intestinal tract and exhibit good antibacterial activity following oral administration would extend still further the valuable therapeutic potential of cefuroxime.

It is known from the literature pertaining to $\beta$-lactam antibiotics that the effect upon oral administration of penicillin antibiotics such as ampicillin can be improved by converting the carboxy group at the 3-position of the penam nucleus to certain esterified carboxy groups; there have also been some proposals that the activity upon oral administration of certain cephalosporin antibiotics may be enhanced by esterification in similar manner. It is believed that the presence of an appropriate esterifying group enhances absorption of the compound from the gastro-intestinal tract, whereupon the esterifying group is hydrolysed by enzymes present in, for example serum and body tissues to yield the antibiotically active parent acid. It will be appreciated that the precise nature of the esterifying group is critical since it is necessary that the ester should be sufficiently stable to allow the ester to reach the site of absorption without undergoing significant degradation, e.g. in the stomach, while on the other hand the ester must be sufficiently susceptible to esterase hydrolysis so that the antibiotically active parent acid is liberated within a short time of the ester being absorbed.

The selection of a particular esterifying group to enhance the effect upon oral administration of a $\beta$-lactam antibiotic will also be influenced by the specific $\beta$-lactam compound chosen. Thus, for example, esterifying groups which have been found effective in improving the activity of orally administered penicillin antibiotics do not necessarily convey similar advantages to antibiotics of the cephalosporin series. An example which may be cited here is the case of pivaloyloxymethyl esters. Thus, the pivaloyloxymethyl ester of, for example, ampicillin is known to improve the oral absorption of ampicillin. The pivaloyloxymethyl ester of cefuroxime on the other hand, exhibits little effect upon oral administration, possibly because the ester is not absorbed from the gastro-intestinal tract or alternatively is substantially resistant to esterase hydrolysis so that the antibiotically active acid is not liberated to any significant extent following absorption.

We have now found that esters of cefuroxime, which may be represented by the formula

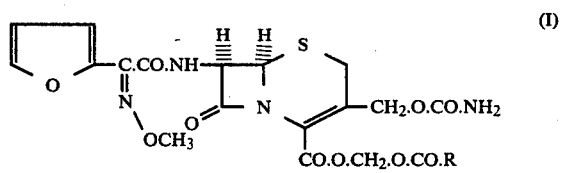

(where R is a primary or secondary alkyl group containing 1 to 4 carbon atoms), possess properties which render these compounds of significant potential value as orally administrable antibiotics. When the group R posseses an asymmetric carbon atom, the individual diastereoisomers of formula as well as mixtures thereof, are embraced by the invention.

Thus the esters (I) possess reasonable stability as evidenced by the fact that they exhibit low antibacterial activity in vitro compared to cefuroxime (this indicates that a high proportion of ester remains unchanged throughout the in vitro tests and so confirms the stability of the esters). The esters are, on the other hand, extremely susceptible to esterase hydrolysis leading to formation of cefuroxime, as evidenced by in vitro tests employing esterases derived from rat liver, human liver and human serum.

In vivo testing in mice, rats and dogs confirms that oral administration of esters of (I) leads to significantly greater absorption of cefuroxime, as evidenced by higher serum levels and increased urinary recovery, than does oral administration of cefuroxime itself.

Of the compounds of formula I the following have been shown to provide particularly good absorption of cefuroxime:

acetoxymethyl (6R,7R)-3-carbamoyloxymethyl-7-[(Z)-2-(fur-2-yl)-2-methoxyiminoacetamido]ceph-3-em-4-carboxylate;

propionyloxymethyl (6R,7R)-3-carbamoyloxymethyl-7-[(Z)-2-(fur-2-yl)-2-methoxyiminoacetamido]ceph-3-em-4-carboxylate;

isobutyryloxymethyl (6R,7R)-3-carbamoyloxymethyl-7-[(Z)-2-(fur-2-yl)-2-methoxyiminoacetamido]ceph-3-em-4-carboxylate; and isovaleryloxymethyl (6R,7R)-3-carbamoyloxymethyl-7-[(Z)-2-(fur-2-yl)-2-methoxyiminoacetamido]ceph-3-em-4-carboxylate.

The compounds (I) may be prepared in conventional manner, for example by reacting cefuroxime or a salt thereof (e.g. an alkali metal salt such as the sodium or potassium salt or an onium salt, e.g. an ammonium for example a quaternary ammonium salt) with a haloester of formula

X.CH₂.O.CO.R   (II)

(where R is as defined above and X is halogen such as chlorine, bromine or iodine). The reaction is conveniently effected in solution in an inert organic solvent (e.g. an N,N-disubstituted amide such as N,N-dimethylformamide or N,N-dimethylacetamide, a ketone such as acetone, a sulphoxide such as dimethylsulphoxide, a nitrile such as acetonitrile, or hexamethyl phosphoric (triamide) at a temperature in the range −50° to +150° C., e.g. −10° to +50° C., conveniently between 0° C. and room temperature. When a cefuroxime salt, for example, the potassium salt, is employed as starting material and the reaction is effected in a nitrile solvent, a crown ether such as, 18-crown-6 may, if desired, be employed. When cefuroxime acid is employed as starting material it may be advantageous to effect the reaction in the presence of a base, e.g. a weak inorganic base such as sodium carbonate or potassium carbonate; it is convenient to add the base to the cefuroxime-containing reaction system prior to addition of the haloester (II). The use of potassium carbonate as base in conjunction with a compound (II) in which X is bromine or iodine has been found advantageous in that under these conditions the formation of a ceph-2-em ester product is minimised. It is convenient to employ substantially equivalent amounts of cefuroxime and base, e.g. about 0.5 moles of a diacidic base such as potassium carbonate per mole of cefuroxime. The haloester (II) is conveniently employed in slight excess, e.g. in an amount of 1–1.5 moles per mole of cefuroxime.

The course of the reaction may readily be monitored by t.l.c., since the process involves conversion of a polar acid or salt starting material to a neutral ester product.

The esters (I) may also be prepared by acylation of a compound of formula

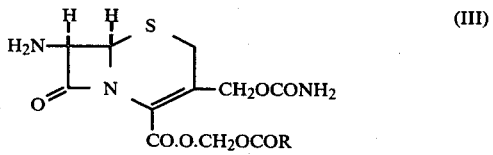
(III)

(wherein R is as hereinbefore defined) or an acid addition salt or N-silyl derivative thereof, using (Z)-2-(fur-2-yl)-2-methoxyiminoacetic acid or a reactive derivative thereof, for example in the manner disclosed in the aforementioned British Pat. No. 1,453,049.

Compounds of formula I may conveniently be prepared by acylating a compound of formula (III) with an acylating agent comprising an acid halide, particularly an acid chloride or bromide, of the said acid. Such acylation may be effected at temperatures of from −50° to +50° C., preferably −20° to +30° C. The acylation may be effected in aqueous or non-aqueous media.

Acylation with an acid halide may be effected in the presence of an acid binding agent (e.g. a tertiary amine such as triethylamine or dimethylaniline, an inorganic base such as calcium carbonate or sodium bicarbonate, or an oxirane, preferably a lower-1,2-alkylene oxide such as ethylene oxide or propylene oxide) which serves to bind hydrogen halide liberated in the acylation reaction.

The free acid may itself be used as the acylating agent. Such acylations are desirably conducted in the presence of, for example, a carbodiimide such as N,N′-dicyclohexylcarbodiimide, a carbonyl compound such as carbonyldiimidazole; or an isoxazolinium salt such as N-ethyl-5-phenylisoxazolinium-3′-sulphonate or n-t-butyl-5-methylisoxazolinium perchlorate. The condensation reaction is desirably effected in an anhydrous reaction medium, e.g. methylene chloride, dimethylformamide or acetonitrile.

Acylation may also be effected with other amide-forming derivatives of the free acid such as, for example, a symmetrical anhydride or a mixed anhydride, e.g. with pivalic acid or formed with a haloformate such as a lower alkyl haloformate. The mixed or symmetrical anhydrides may be generated in situ. Thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluenesulphonic acid).

The above described starting materials of formula (III) may be prepared in a conventional manner, for example, using the techniques described in U.S. Pat. No. 3,905,963 and British Patent Specifications Nos. 1,041,985 and 1,350,772.

If the desired ester product is significantly contaminated by the corresponding ceph-2-em isomer the product may be oxidised (e.g. by treatment with a peracid such as metaperiodic acid, peracetic acid, monoperphthalic acid or m-chloroperbenzoic acid or with t-butyl hypochlorite in the presence of a weak base such as pyridine) to give the ceph-3-em 1-oxide ester, which may then be reduced (e.g. by treatment with acetyl chloride and potassium iodide) to yield substantially pure ceph-3-em ester.

It may be desirable to purify the haloester (II) before use, e.g. by distillation or selective hydrolysis, to remove impurities such as compounds of formula

X.CH₂.O.CH₂.X   (IV)

(where X is as defined above).

The esters of formula I may be formulated as compositions for oral administration in conventional manner, with the aid of any necessary pharmaceutical carriers or excipients. The compositions are conveniently prepared as tablets, capsules or sachets, advantageously in unit dose form, and may contain conventional excipients such as binding agents, fillers, lubricants, disintegrants and wetting agents. Tablets may be coated in conventional manner. The active compounds may further be formulated in rectal composition such as suppositories or retention enemas.

The compositions may contain from 0.1% upwards, e.g. 0.1–99% conveniently from 10–60% of the active ingredient (I), depending on the method of administration. Compositions in dosage unit form conveniently contain 50–500 mg of the active ingredient (calculated as cefuroxime). Doses employed for adult human treatment will typically be in the range 500–5000 mg per day, e.g. 1500 mg per day, (calculated as cefuroxime), although the precise dose will depend on, inter alia, the frequency of administration.

The following examples illustrate the invention. All temperatures are in °C. The potassium carbonate employed was dried at 120° in vacuo and finely ground. The N,N-dimethylformamide employed was dried by passage through acidic alumina. In Examples 4 and 5 the melting points were determined by the capillary method and are uncorrected.

EXAMPLE 1

Acetoxymethyl (6R,7R)-3-carbamoyloxymethyl-7-[(Z)-2-(fur-2-yl)-2-methoxyiminoacetamido]ceph-3-em-4-carboxylate A solution (6R,7R)-3-carbamoyloxymethyl-7-[(Z)-2-(fur-2-yl)-2-methoxyiminoacetamido]ceph-3-em-4-carboxylic acid (12.00 g) in N,N-dimethylformamide (70 ml) was stirred for 10 minutes with potassium carbonate (1.95 g), during which time the mixture became darker and the solid almost completely dissolved. A solution of acetoxymethyl bromide (5.0 g) in N,N-dimethylformamide (15 ml) was then added, whereupon precipitation of potassium bromide occurred almost immediately. The reaction mixture was stirred at 21° for 30 minutes, after which it is shown by t.l.c. (developing with chloroform:acetone=2:1 and observing the spots under u.v. light and by spraying with ninhydrin and heating to 120°) to contain no unreacted cephalosporin starting material. The reaction mixture was then poured into a mixture of 2 N-hydrochloric acid (350 ml) and ethyl acetate (350 ml), and the aqueous phase was extracted with further ethyl acetate (2×200 ml). The organic extracts were combined and were washed successively with 2 N-hydrochloric acid (2×300 ml), water (2×300 ml), aqueous sodium bicarbonate solution (3%, 300 ml), water (3×300 ml), and saturated sodium chloride solution (2×300 ml), and dried (MgSO$_4$), and the solvent was removed in vacuo to give a yellow froth (13.87 g). This product was absorbed onto a column of silica gel (Hopkin and Williams, 100 to 200 mesh-330 g) which was eluted with chloroform:acetone=2:1; 25 ml fractions were collected. Evaporation of fractions 11 to 32 gave crude title ester, which crystallised during the evaporation. The resulting solid (7.217 g) was triturated with ether to give the title ester (6.58 g) as a white powder, m.p. 181° to 183° (Kofler); $[\alpha]_D+58°$ (c 0.98, DMSO), $[\alpha]_D+72°$ (c 1.32, dioxan); $\lambda_{max}$ (EtOH) 276 nm ($\epsilon$ 19,750). The nmr and infrared data are shown in Table 1 hereinafter. The structure of the product was also confirmed by microanalysis.

EXAMPLE 2

Propionyloxymethyl (6R,7R)-3-carbamoyloxymethyl-7-[(Z)-2-(fur-2-yl)-2-methoxyiminoacetamido]ceph-3-em-4-carboxylate (a) Potassium carbonate (690 mg) was stirred for 30 minutes with a solution of (6R,7R)-3-carbamoyloxymethyl-7-[(Z)-2-(fur-2-yl)-2-methoxyiminoacetamido]-ceph-3-em-4-carboxylic acid (4.24 g) in N,N-dimethylformamide (25 ml). A solution of chloromethyl propionate (1.226 g) in N,N-dimethylformamide (1 ml) was added to the resulting dark brown solution and the reaction mixture was stirred for 20 hours and poured into 2 N-hydrochloric acid (200 ml) to give a brown solid which dissolved on addition of ethyl acetate (200 ml). The organic phase was separated, washed with saturated aqueous sodium bicarbonate solution (200 ml), dried (MgSO$_4$) and evaporated to a brown foam, which on trituration with di-isopropyl ether (75 ml) afforded a brown solid which was filtered off, washed with more di-isopropyl ether and dried to give the title ester contaminated with ca. 55% of the corresponding ceph-2-em-isomer (by n.m.r. estimation), as a pale brown powder (3.915 g).

(b) A solution of m-chloroperbenzoic acid (1.424 g) in dichloromethane (20 ml) was added to a solution of the product from (a) above (3.82 g) in dichloromethane (100 ml) at ca. 0°, immediately causing the separation of a brown gel. After 10 minutes the mixture was allowed to warm up to room temperature and after a further 20 minutes the mixture was evaporated in vacuo. The resulting yellow solid was triturated with ether, filtered and washed with ether to give propionyloxymethyl (1R and 1S, 6R,7R)-3-carbamoyloxymethyl-7-[(Z)-2-(fur-2-yl)-2-methoxyiminoacetamido]ceph-3-em-4-carboxylate, 1-oxides as a pale powder (3.696 g), m.p. 175°–177° (decomp.); $[\alpha]_D^{19}+80°$ (c 0.5, DMSO). The structure of this product was confirmed by i.r. and n.m.r. spectroscopy and by microanalysis.

(c) A solution of the product from (b) above (3.592 g) in N,N-dimethylformamide (15 ml) was treated with potassium iodide (4.53 g) and the mixture was cooled to $-10°$, whereupon acetyl chloride (1.02 ml) was added. The ensuing reaction appeared to be complete after 30 minutes (by t.l.c.), and the reaction mixture was then added dropwise into aqueous sodium metabisulphite solution (3% w/v, 300 ml) to yield a precipitate which was filtered off and dissolved in ethyl acetate (100 ml). The organic solution was washed successively with 2 N-hydrochloric acid (100 ml) and saturated aqueous sodium bicarbonate (100 ml) and was then dried (MgSO$_4$) and evaporated in vacuo to give a cream solid. This product was subjected to column chromatography on Kieselgel 60 silica (100 g), elution being carried out with chloroform:acetone (12:1). Appropriate fractions were combined and evaporated in vacuo to afford a pale yellow foam (2.226 g) which was triturated with di-isopropyl ether, filtered and dried to give the title compound (2.108 g) as a very pale yellow powder, m.p. 94°–103°; $[\alpha]_D^{20}+36°$ (c 1, DMSO); $\lambda_{max}$ (EtOH) 277 nm ($\epsilon$ 17,660). The n.m.r. and infrared data are shown in Table 1 hereinafter. The n.m.r. spectrum indicated that some ceph-2-em isomer was still present. The structure of the product was also confirmed by microanalysis.

EXAMPLE 3

Propionyloxymethyl (6R,7R)-3-carbamoyloxymethyl-7-(Z)-2-(fur-2-yl)-2-methoxyiminoacetamido]ceph-3-em-4-carboxylate A solution of chloromethyl propionate (4.88 g, 40 mmole) in acetone (10 ml) was added to a solution of sodium iodide (18 g, 120 mmole) in acetone (70 ml); cloudiness instantly resulted. The reaction mixture was refluxed (30 minutes) and then evaporated in vacuo to give a dark solid.

This solid was partially dissolved in purified N,N-dimethylformamide (50 ml), and the resultant mixture was treated with a solution of potassium (6R,7R)-3-carbamoyloxymethyl-7-[(Z)-2-(fur-2-yl)-2-methoxyiminoacetamido]ceph-3-em-4-carboxylate (9.24 g 20 mmole) in purified N,N-dimethylformamide (50 ml).

T.l.c. after ca 10 minutes indicated absence of cephalosporin starting material so after 20 minutes the reaction mixture was poured into 2 N hydrochloric acid (1 liter) to give a brown precipitate which dissolved on addition of ethyl acetate (500 ml). The dark organic layer was separated and washed successively with saturated aqueous sodium bicarbonate solution (500 ml) and sodium metabisulphite solution (500 ml) (this gave a pale yellow organic layer) and evaporated in vacuo to give a viscous brown oil which crystallised to a pale yellow solid. Trituration of this solid with di-isopropyl ether (150 ml) gave a pale solid which was filtered off and washed with fresh di-isopropyl ether and dried in vacuo to give the title ester (7.00 g) as a white powder m.p. 170° to 174° (dec) $[\alpha]_D + 49°$ (c 1.0, DMSO), $\lambda_{max}$ (EtOH) 276 nm ($E_{1\,cm}^{1\%}$ 378, $\epsilon$ 19,300). [Found: C, 47.4; H, 4.5; N, 10.7; S, 6.4; $C_{20}H_{22}N_4O_{10}S$ (510.48) requires C, 47.05; H, 4.3; N, 11.0; S, 6.3%].

The n.m.r. and infrared data are shown in Table 1 hereinafter.

Preparation of starting materials:

PREPARATION 1

Chloromethyl Isobutyrate

2-Methylpropanoyl chloride (10.2 g) was added to paraformaldehyde (1.86 g, 56 mmole) containing a little zinc chloride and the mixture was heated to reflux for 40 minutes. During this time the paraformaldehyde dissolved and the mixture turned brown. The supernatant liquid was decanted from the zinc chloride and distillation afforded the title ester (3.45 g) b.p. 45° to 56°/40 mm which was characterised by its nmr ($CDCl_3$) and infrared ($CHBr_3$) spectra.

PREPARATION 2

Bromomethyl 3-methylbutanoate

3-Methylbutanoyl bromide (3.48 g, 21 mmole) was added to paraformaldehyde (630 mg, 21 mmole) and the mixture was refluxed for 15 minutes during which time the paraformaldehyde dissolved. The resultant pale brown liquid was distilled under reduced pressure to give the title ester (1.89 g) as a colourless liquid, b.p. 80° to 82°/37 mm, which was characterised by its nmr ($CDCl_3$) and infrared ($CHBr_3$). spectra.

EXAMPLE 4

Isobutyryloxymethyl (6R,7R)-3-carbamoyloxymethyl-7-[(Z)-2-(fur-2-yl)-2-methoxyiminoacetamido]-ceph-3-em-4-carboxylate Chloromethyl isobutyrate (2.04 g, 15 mmole) in acetone (45 ml) was mixed with sodium iodide (6.75 g, 45 mmole) and the mixture refluxed for 30 minutes. Evaporation in vacuo gave the iodomethyl ester (3.95 g) as a dark red oil. (6R,7R)-3-Carbamoyloxymethyl-7-[(Z)-2-(fur-2-yl)-2-methoxyiminoacetamido]ceph-3-em-4-carboxylic acid, potassium salt (5.52 g, 12 mmole) was added to a solution of the above iodomethyl ester (3.9 g) in pure N,N-dimethylformamide (35 ml) producing a dark solution. After 20 minutes the reaction mixture was poured into 2 N hydrochloric acid (350 ml) to give a yellow solid which dissolved on addition of ethyl acetate (350 ml). The organic phase was separated and washed with saturated sodium bicarbonate solution (350 ml), sodium metabisulphite solution (350 ml) and brine (200 ml), dried over magnesium sulphate and evaporated in vacuo to give a yellow foam. The foam was triturated with di-isopropyl ether (50 ml), filtered and washed with fresh di-isopropyl ether and dried to give the title compound (5.344 g) as a yellow powder, m.p. 67° to 74°; $[\alpha]_D^{22} + 37°$ (c 1.0, DMSO); $\lambda_{max}$(EtOH) 277 nm ($E_{1\,cm}^{1\%}$ 362; $\epsilon$ 18,985); [Found: C, 47.9; H, 4.9; N, 10.15; S, 6.0; $C_{21}H_{24}N_4O_{10}S$ (524.5) requires C, 48.1; H, 4.6; N, 10.7; S, 6.1%].

The nmr and infrared data are shown in Table 1 hereinafter.

EXAMPLE 5

Isovaleryloxymethyl (6R,7R)-3-carbamoyloxymethyl-7-[(Z)-2-(fur-2-yl)-2-methoxyiminoacetamido]ceph-3-em-4-carboxylate Bromomethyl 3-methylbutanoate (1.328 g, 6.7 mmole) was added to a solution of (6R,7R)-3-carbamoyloxymethyl-7-[(Z)-2-(fur-2-yl)-2-methoxyiminoacetamido]ceph-3-em-4-carboxylic acid, potassium salt (2.772 g, 6 mmole) in purified N,N dimethylformamide (18 ml). The mixture was allowed to react for 15 minutes and was then worked up as described in Example 4 to give the slightly impure title compound (2.809 g).

A portion (2.75 g) of the title compound was subjected to column chromatography (on Kieselgel 60, 60 g); elution was with chloroform:acetone (7:1). The desired fractions were combined and evaporated in vacuo to yield a pale yellow foam which, on trituration with di-isopropyl ether, afforded a white solid which was filtered and washed with fresh di-isopropyl ether and dried in vacuo to give the pure title compound (2.095 g) as a white powder m.p. 66° to 73°; $[\alpha]_D^{21} + 74.5°$ (c 1.0, DMSO); $\lambda_{max}$ (EtOH) 277.5 nm ($E_{1\,cm}^{1\%}$ 348; $\epsilon$ 18,740); [Found: C, 47.7; H, 4.9; N, 10.0; S, 5.8; $C_{22}H_{26}N_4O_{10}S$ (538.5) requires C, 49.05; H, 4.9; N, 10.4; S, 5.95%]. The nmr and infrared data are shown in Table 1 hereinafter.

TABLE 1

Physical Properties of the products of Examples 1-5

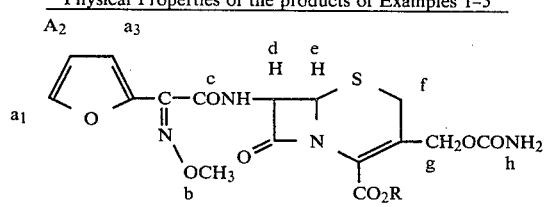

| Example No. | Solvent | $\tau$ (100 MHz; JHz) | | | | | | | | | Assignments for |
|---|---|---|---|---|---|---|---|---|---|---|---|
| | | $a_{1,2,3}$ | b | c | d | e | f | g | h | R | R $\tau$ |
| 1 | DMSO-$d_6$ | 2.16 (m) 3.29 (m) | 6.09 | 0.20 (d9) | 4.16 (dd 9,5) | 4.74 d(5) | 6.27 6.48 (J18) | 5.10 5.39 (J13) | 3.36 | —CH$_2$OCCH$_3$ (with C=O) i j | i 4.11 4.19 (m) j 7.90 (s) |
| 2 | DMSO-$d_6$ | 2.18 3.2 to 3.5 (m) | 6.10 | 0.24 (d8) | 4.08 (dd) | 4.75 (d5) | 6.40 | 5.12 5.40 (J14) | obscured by $a_2$ and $a_3$ | —CH$_2$OCCH$_2$CH$_3$ (with C=O) i j k | i 4.08 j 7.54 (q7) k 8.92 (t7) |

TABLE 1-continued

Physical Properties of the products of Examples 1-5

$$\text{furan}(a_1, A_2, a_3) - \underset{\underset{\underset{OCH_3}{N}}{\overset{c}{\|}}}{C} - CONH - \underset{\overset{d}{H}}{\overset{}{C}} - \underset{\overset{e}{H}}{\overset{}{C}} \cdots S \cdots CH_2OCONH_2 \text{ (g, h)}, CO_2R$$

| No | Solvent | | | | | | | | | | | |
|----|---------|---|---|---|---|---|---|---|---|---|---|---|
| 3 | DMSO-d6 | 2.20 (m) 3.35 (m) | 6.12 | 0.24 (d8) | 4.15 (m) | 4.77 (d5) | 6.28 6.48 (J18) | 5.15 5.44 (J13) | 3.40 | —CH$_2$OCCH$_2$CH$_3$ (i, j, k) with O double bond | i 4.15 (m) j 7.60 (q8) k 8.96 (t8) |
| 4 | DMSO-d6 | 2.16 (m) 3.2 to 3.4 (m) | 6.10 | 0.21 (d9) | 4.13 (dd 9,5) | 4.74 (d5) | 6.38 (s) | 5.11 5.39 (J12) | 3.38 | —CH$_1$OCCH(CH$_3$k)$_2$ | i 4.07 4.17 $J=6$ j 7.38 (m) k 8.87 (d7) |
| 5 | DMSO-d6 CDCl$_3$ | 2.10 3.2 to 3.4 (m) | 6.07 | 0.16 (d9) | 4.08 (dd 9,5) | 4.70 (d5) | 6.24 6.46 (J18) | 5.07 5.35 (J12) | 3.36 | —CH$_2$OCCH$_2$CH(CH$_3$l)$_2$ | i 4.05 4.13 $J=6$ j 7.70 (d7) k 7.96 (m) l 9.05 (d7) |

| Example No | Solvent | $\nu_{max}$ (cm$^{-1}$) | | | | |
|---|---|---|---|---|---|---|
| | | NH$_2$ and NH | β-lactam | CO$_2$R | OCONH$_2$ | CONH |
| 1 | Nujol | 3452 3420 | 1780 | 1730 | 1708 | 1660 1528 |
| 2 | CHBr$_3$ | 3565 3440 | 1786 | 1756 1740 | obscured | 1692 1520 |
| 3 | CHBr$_3$ | 3500 3390 | 1785 | 1745 1730 | obscured | 1680 1530 |
| 4 | CHBr$_3$ | 3510 3390 | 1778 | 1740 1730 | 1720 1576 | 1680 1512 |
| 5 | CHBr$_3$ | 3530 3400 | 1784 | 1754 1730 | 1730 1582 | 1684 1520 |

EXAMPLE A

Tablet

Composition:

| | |
|---|---|
| Acetoxymethyl (6R, 7R)-3-carbamoyloxymethyl-7-[(Z)-2-(fur-2-yl)-2-methoxyimino-acetamido]ceph-3-em-4-carboxylate (micronised) | 292.5 mg |
| Sodium starch glycolate (Primojel) | 7.0 mg |
| Microcrystalline cellulose (Avicel PH 101) | 48.75 mg |
| Magnesium stearate | 1.75 mg |
| Total weight: | 350.0 mg |

Method of preparation

The magnesium stearate was blended with the active ingredient and tablet slugs were prepared by direct compression. The slugs were broken down through 12 mesh, 16 mesh and 20 mesh consecutively and the granules were blended with the sodium starch glycolate and microcrystalline cellulose. The blend was compressed on 10.5 mm diameter normal concave punches to a tablet weight of 350 mg. The tablets may be film coated by the aqueous or organic solvent method using cellulose derivatives with plasticiser and colouring matter.

As an alternative to the preliminary slugging stage the active ingredient may be densified by roller compaction.

EXAMPLE B

Powder for oral suspension (in sachet)

Composition (per sachet).

| | |
|---|---|
| Acetoxymethyl (6R, 7R)-3-carbamoyloxymethyl-7-[(Z)-2-(fur-2-yl)-2-methoxyimino-acetamido]ceph-3-em-4-carboxylate (milled) | 292.5 mg |
| Sodium carboxymethyl cellulose (low viscosity) | 90 mg |
| Sunset yellow FCF | 5 mg |
| Spray-dried orange flavour | 150 mg |
| Caster sugar | 2.2 g |

Method of preparation

The active ingredient was milled (using a fluid energy mill) and blended intimately with the sodium carboxymethyl cellulose, the flavour ingredient and the colouring agent. This blend was then further blended with the caster sugar, adding the latter in two stages. The required weight was transferred to a paper/aluminium/polythene sachet and sealed by heat. The contents of each sachet were intended for constitution in about 15 mls of water, shortly before administration.

We claim:

1. The syn isomer of a cephalosporin antibiotic of the formula

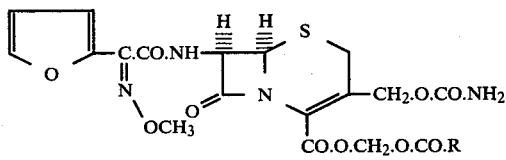

(where R is a primary or secondary alkyl group containing 1 to 4 carbon atoms).

2. A compound as claimed in claim 1 wherein R is a primary or secondary alkyl group containing 3 or 4 carbon atoms.

3. The compound of claim 1 which is acetoxymethyl (6R,7R)-3-carbamoyloxymethyl-7-[(Z)-2-(fur-2-yl)-2-methoxyiminoacetamido]ceph-3-em-4-carboxylate.

4. The compound of claim 1 which is propionyloxymethyl (6R,7R)-3-carbamoyloxymethyl-7[(Z)-2-(fur-2-yl)-2-methoxyiminoacetamido]ceph-3-em-4-carboxylate.

5. The compound of claim 1 which is isobutyryloxymethyl (6R,7R)-3-carbamoyloxymethyl-7-[(Z)-2-(fur-2-yl)-2-methoxyiminoacetamido]ceph-3-em-4-carboxylate.

6. The compound of claim 1 which is isovaleryloxymethyl (6R,7R)-3-carbamoyloxymethyl-7-[(Z)-2-(fur-2-yl)-2-methoxyiminoacetamido]ceph-3-em-4-carboxylate.

* * * * *